(12) United States Patent
Oguma

(10) Patent No.: US 7,123,956 B2
(45) Date of Patent: Oct. 17, 2006

(54) VISCERAL FAT ESTIMATION APPARATUS

(75) Inventor: Koji Oguma, Fujisawa (JP)

(73) Assignee: Tanita Corporation, Tokyo (JP)

( * ) Notice: Subject to any disclaimer, the term of this patent is extended or adjusted under 35 U.S.C. 154(b) by 256 days.

(21) Appl. No.: 10/280,040

(22) Filed: Oct. 25, 2002

(65) Prior Publication Data

US 2003/0083589 A1 May 1, 2003

(30) Foreign Application Priority Data

Oct. 31, 2001 (JP) .................................... 2001-335111

(51) Int. Cl.
*A61B 5/05* (2006.01)

(52) U.S. Cl. ........................................... 600/547
(58) Field of Classification Search ............. 600/547, 600/587, 483; 128/921, 920; 705/2; 700/90; 708/100

See application file for complete search history.

(56) References Cited

U.S. PATENT DOCUMENTS

| 5,579,782 A | 12/1996 | Masuo ....................... 128/734 |
| 2002/0123695 A1 | 9/2002 | Kawanisihi ................. 600/547 |

FOREIGN PATENT DOCUMENTS

| EP | 0700661 A1 | 3/1996 |
| EP | 1063500 A2 | 12/2000 |
| EP | 1219238 A1 | 7/2002 |
| EP | 1 283 633 | 9/2002 |
| JP | 2001161670 | 6/1991 |
| JP | 5-49050 | 7/1993 |
| JP | 07-175404 | 7/1995 |
| JP | 10-295651 | 11/1998 |
| JP | 11-265351 | 9/1999 |
| WO | WO 0115601 A1 | 3/2001 |
| WO | WO 0178600 A1 | 10/2001 |

*Primary Examiner*—Mary Beth Jones
*Assistant Examiner*—Brian Szmal
(74) *Attorney, Agent, or Firm*—McDermott Will & Emery LLP

(57) ABSTRACT

Disclosed is a visceral fat estimation apparatus, comprising: an input device: an estimation device; a target calorie intake determination device; a calorie consumption determination device; an allowable calorie intake update device; and a calorie consumption device. According to the present invention the input device enters at least height, body weight and body fat rate of a person to be measured, and the estimation device estimates a visceral fat area based in the input value entered by the input device. Furthermore, the target calorie intake determination device determines a target calorie intake for a day, and the calorie consumption determination device determines a calorie to be consumed due to an exercise for a day. The allowable calorie intake update device updates an allowable calorie intake for a day, and the calorie consumption update device updates a calorie to be consumed due to an exercise for a day.

12 Claims, 15 Drawing Sheets

| | HEIGHT | AGE |
|---|---|---|
| | 162cm | 36 YEARS OLD |
| | 71cm | 63.4kg |
| | WAIST | BODY WEIGHT |

BODY FAT RATE 36.7%

116cm$^2$

VISCERAL FAT AREA

TARGET VALUE

100cm$^2$

VISCERAL FAT AREA

JOGGING (NORMAL SPEED)

JOGGING (FAST SPEED)

10 min.  74.2 kcal

INTAKE: 457kcal

EXERCISE: 126kcal

PRECEDING DAY: +87kcal

LACK OF EXERCISE

AMOUNT IN REDUCTION OF
VISCERAL FAT AREA:−0.5cm²

VISCERAL FAT ESTIMATION APPARATUS

BACKGROUND OF THE INVENTION

1. Field of the Invention

The present invention relates to a visceral fat estimation apparatus for estimating a visceral fat of a person to be measured.

2. Prior Art

Various types of apparatus for measuring a body fat of a person that is considered as the cause of adiposity have been known in the art. For example, Japanese Patent Publication No. 5-49050 discloses a body fat weight meter in which a personal data such as sex, height and age is entered and measurement of body weight and impedance between extreme parts of the body is performed for estimating the weight of fat tissue in a whole body. Also known in the art is an MRI apparatus or an X-ray CT apparatus in which a tomogram of an abdomen (or a navel region) of the body is taken and an analysis of the picture is performed to derive a subcutaneous fat area or a visceral fat area.

Furthermore, several types of calorie calculators for promptly calculating calorie intake and calorie consumption due to an exercise have been proposed for the purpose of curing any adiposity.

In this connection the adiposity is divided into two types: subcutaneous fat type and visceral fat type. Recently it becomes more important to know the amount of visceral fat due to the fact that it greatly contributes to onset of adult noncomminicable disease. Therefore, it is necessary to determine whether the adiposity is of subcutaneous fat type or of visceral fat type.

Unfortunately the prior art apparatus as described above are defective in the following point of view: The body fat weight meter provides the body fat mass and body fat rate only in a whole body. The MRI and X-ray CT apparatus are expensive in cost. In addition, an expert person is necessary for positioning a person to be measured so that he lies facing upward and keeps such posture during the period of measurement. Accordingly, the person to be measured can't operate the apparatus by himself, which means that the apparatus is not suitable for home use. Furthermore, the apparatus is bulky and cumbersome in handling. It takes longer period of time for measurement. In particular, during the measurement using the X-ray CT apparatus, the person to be measured may be subjected to exposure of radiation that is lower in dose, not substantially affected to the health. Therefore, the person is not mentally willing to have the measurement using the X-ray. Moreover, any repetition of several times of such measurement is not allowable because of accumulation in dose of exposure of radiation.

On the other hand, the calorie calculator in the prior art has capability of simply calculating the calorie value, but has nothing associated with the body fat meter. In order to cure any adiposity it is highly desire to have some function of associating the calorie control with the visceral fat meter in such manner that the current value of visceral fat area or body fat rate can be measured; if it falls within the region of adiposity then the target value of visceral fat area or body fat rate can be set; and the further target value of calorie intake and calorie consumption to attain said target value can be set. There are some apparatus available in the market having capability of setting the target value of body fat rate and calorie consumption, but none of them provide function of additionally setting the target value of calorie intake and visceral fat area.

In view of the above an object of the present invention is to provide a new and improved apparatus for estimating visceral fat in which measurement of visceral fat can easily be made; if it falls within the region of adiposity then the target value of visceral fat area can be set; and the calorie intake and the calorie consumption can be controlled to attain said target value.

SUMMARY OF THE INVENTION

According to one aspect of the present invention there is provided a visceral fat estimation apparatus, comprising: an input device; an estimation device; a target calorie intake determination device; a calorie consumption determination device; an allowable calorie intake update device; and a calorie consumption update device, wherein said input device enters at least height, body weight and body fat rate of a person to be measured; said estimation device estimates a visceral fat area based on the input value entered by said input device; said target calorie intake determination device determines a target calorie intake for a day; said calorie consumption determination device determines a calorie to be consumed due to an exercise for a day; said allowable calorie intake update device updates an allowable calorie intake for a day; and said calorie consumption update device updates a calorie to be consumed due to an exercise for a day.

According to one embodiment of the present invention said input device for entering the height is a height meter.

According to another embodiment of the present invention said input device for entering the height is a keying device that manually enters the height.

According to further embodiment of the present invention said input device for entering the body weight is a weight sensor.

According to yet further embodiment of the present invention said input device for entering the body weight is a keying device that manually enters the body weight.

According to yet further embodiment of the present invention said input device for entering the body fat rate is a body fat meter.

According to yet further embodiment of the present invention said input device for entering the body fat rate is a keying device that manually enters the body fat rate.

According to yet further embodiment of the present invention said calorie consumption determination device determines the calorie to be consumed due to an exercise for a day based on any one of the target values for visceral fat area, body fat rate and body weight and on the time period during which the target value is to be attained.

According to another aspect of the present invention there is provided a visceral fat estimation apparatus, comprising: an input device; an estimation device; a target selection and assignment device; a calorie determination device; a calorie intake determination device; a calorie consumption determination device; a total calorie calculation device; and a display device, wherein said input device enters at least height, body weight and body fat rate of a person to be measured; said estimation device estimates a visceral fat area based on the input value entered by said input device; said target selection and assignment device selects any one of at least visceral fat area, body fat rate and body weight as a subject for reduction and assigns the target value for the selected subject; said calorie determination device determines the calorie value to be consumed for a day based on the estimated visceral fat area, the selected subject and the assigned target value; said calorie intake determination device determines the calorie intake based on the name of food that has been eaten and an amount of intake of the food; said calorie consumption determination device determines the calorie consumption based on the name of exercise that has been done and a time period during which the exercise has been done; said total calorie calculation device calculates the total calorie based on the calorie intake, the calorie consumption and the basal metabolism for the person; and said display device displays an advice message based on the calculated total calorie.

BRIEF DESCRIPTION OF THE DRAWINGS

Now, the present invention will be described in more detail with reference to the accompanying drawings, in which.

DESCRIPTION OF THE PREFERRED EMBODIMENTS

Figure 1:
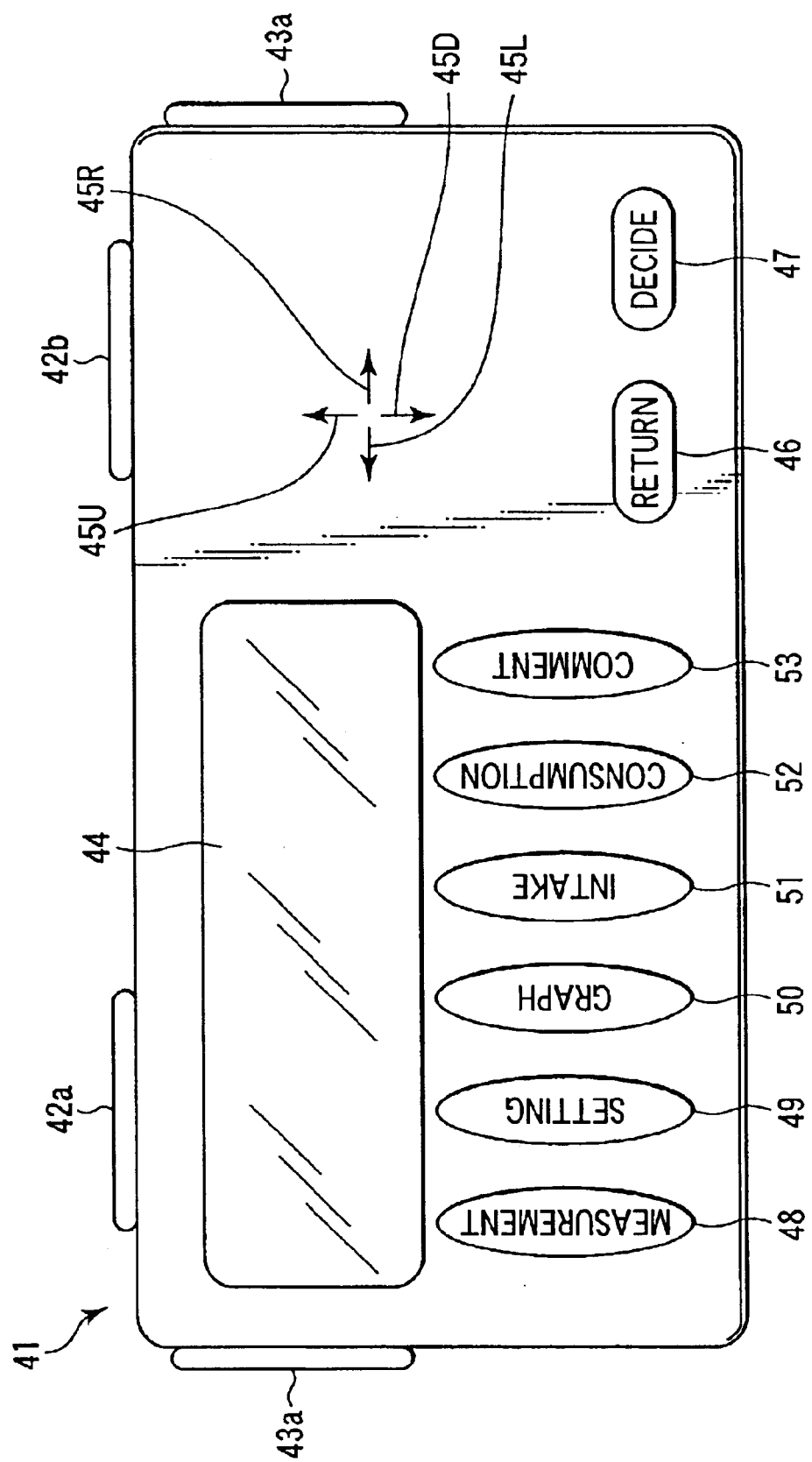
FIG. 1 is a front elevation view of a visceral fat estimation apparatus according to one embodiment of the present invention.

FIG. 1 is a front elevation view of a visceral fat estimation apparatus according to one embodiment of the present invention.

Figure 2:
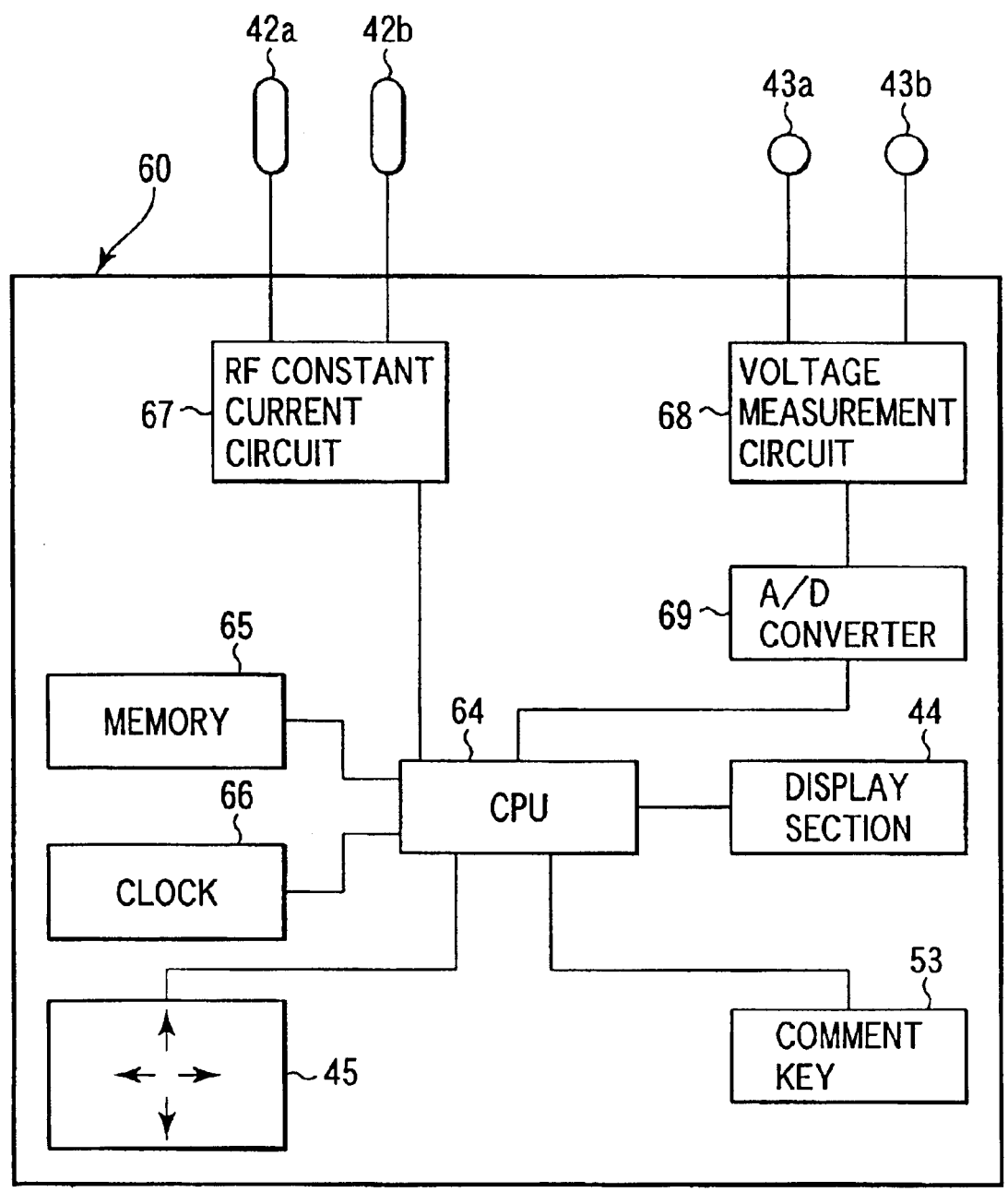
FIG. 2 is a block diagram illustrating an electrical circuit configuration of the visceral fat estimation apparatus in FIG. 1.

FIG. 2 is a block diagram illustrating an electrical circuit configuration of the visceral fat estimation apparatus in FIG. 1. The visceral fat estimation apparatus 41 according to this embodiment comprises: current supplying electrodes 42a, 42b for forming a current path in a living body; voltage detection electrodes 43a, 43b for detecting potential difference across the living body; "↑" key 45U, "↓" key 45D, "→" key 45R and "←" key 45L all for altering the numerical value; a return key 46 for returning to the previous value; a decision key 47 for proceeding to the next item; a measurement key 48 for effecting measurement; a set key 49 for setting the target value of visceral fat area, etc.; a graph key 50 for graphically showing any daily change in measurement result and arithmetic result; an intake key 51 for setting the condition under which the calorie intake is calculated; a consumption key 52 for setting the condition under which the calorie consumption is calculated; a comment key 53 for calculating an allowable calorie intake and the calorie to be consumed due to an exercise for that day; and a display section 44 for displaying the setting condition and the calculation result.

The current supplying electrodes 42a, 42b are positioned on an upper surface of the visceral fat estimation apparatus, and the voltage detection electrodes 43a, 43b are positioned on side surfaces of the apparatus. When the measurement is performed a thumb finger of a left hand of a person to be measured is contact with the current supplying electrode 42a, and a thumb finger of a right hand of the person is contact with the current supplying electrode 42b. Furthermore, a palm of the left hand is contact with the voltage detection electrode 43a, and a palm of the right hand is contact with the voltage detection electrode 43b.

The apparatus 41 further has an electronic circuit board 60 mounted therein. On the circuit board 60 there are mounted the following components: the display section 44; a radio frequency (RF) constant current circuit 67 for supplying a weak RF constant current to the current supplying electrodes 42a, 42b; a voltage measurement circuit 68 for detecting a potential difference for the living body across the voltage detection electrodes 43a, 43b; an A/D converter circuit 69 for converting an analogue signal from the voltage measurement circuit 68 into a digital signal; a clock 66; a memory 65 for storing the setting condition and the calculation result, etc.; and a CPU 64 for processing the control and arithmetic operation of body fat rate and visceral fat area based on the measurement condition and the living body impedance measurement data.

Figure 3:
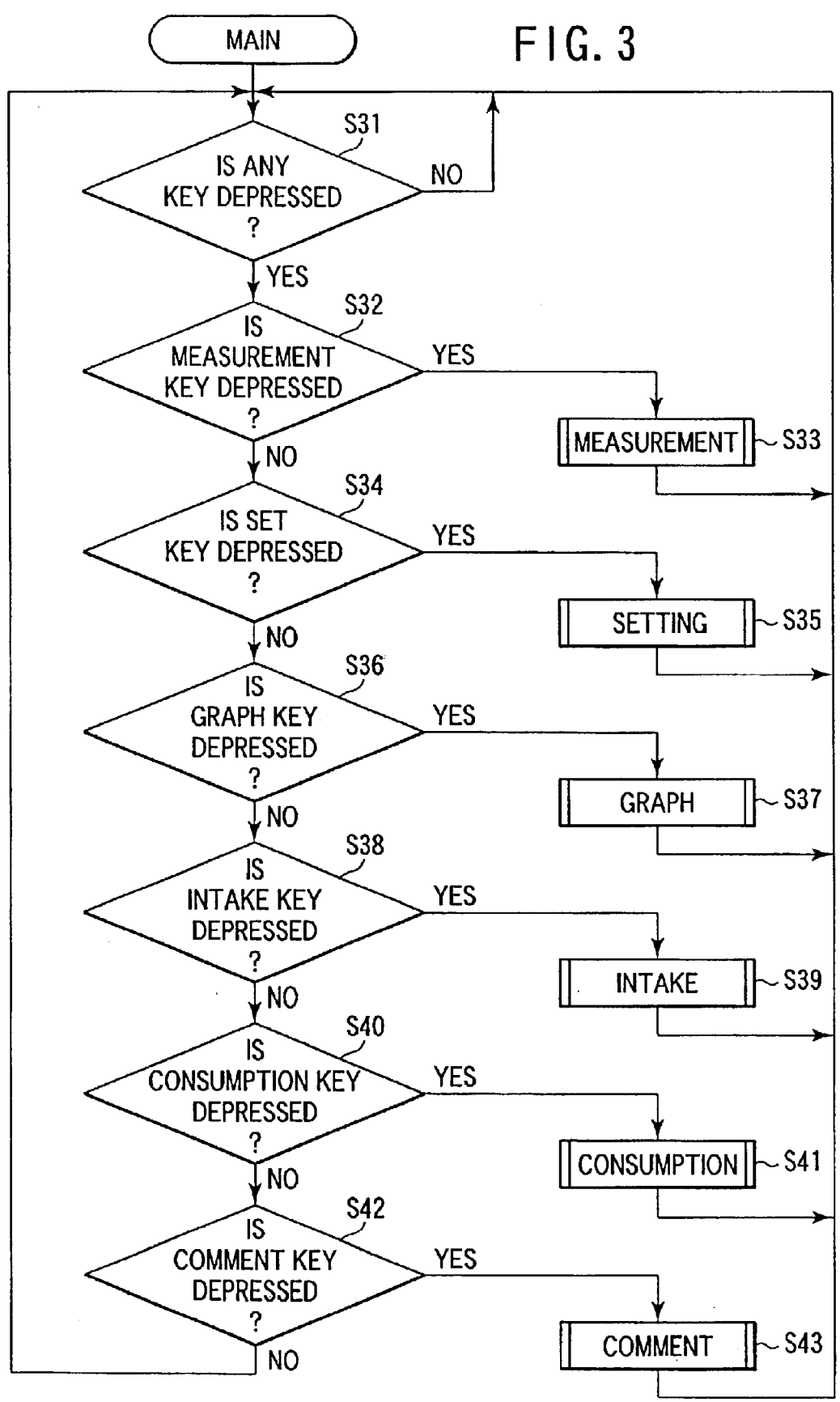
FIG. 3 is a flow chart illustrating a main program routine for the visceral fat estimation apparatus in FIG. 1.

Next, measurement operation for estimating the visceral fat according to the embodiment will be summarized. First of all, when a battery is installed, setting of the current date and time is requested. The setting is done to initialize the clock 66. FIG. 3 is a flow chart illustrating a main program routine for the visceral fat estimation apparatus in FIG. 1. At first step S31 a check is made to determine whether any one of the keys is depressed. If not, the routine returns to step S31. But, if so, the power supply is turned ON. Then, at step S32 it is determined whether the measurement key 48 is depressed or not. If so, the measurement is performed in step S33, and the routine returns to step S31. At step S34 it is determined whether the set key 49 is depressed or not. If so, the setting is performed in step S35, and the routine returns to step S31. At step S36 it is determined whether the graph key 50 is depressed or not. If so, the graph process is performed in step S37, and the routine returns to step S31. At step S38 it is determined whether the intake key 51 is depressed or not. If so, the intake process is performed in step S39, and the routine returns to step S31. At step S40 it is determined whether the consumption key 52 is depressed or not. If so, the consumption process is performed in step S41, and the routine returns to step S31. At step S42 it is determined whether the comment key 53 is depressed or not. If so, the comment process is performed in step S43, and the routine returns to step S31.

Figure 4A:
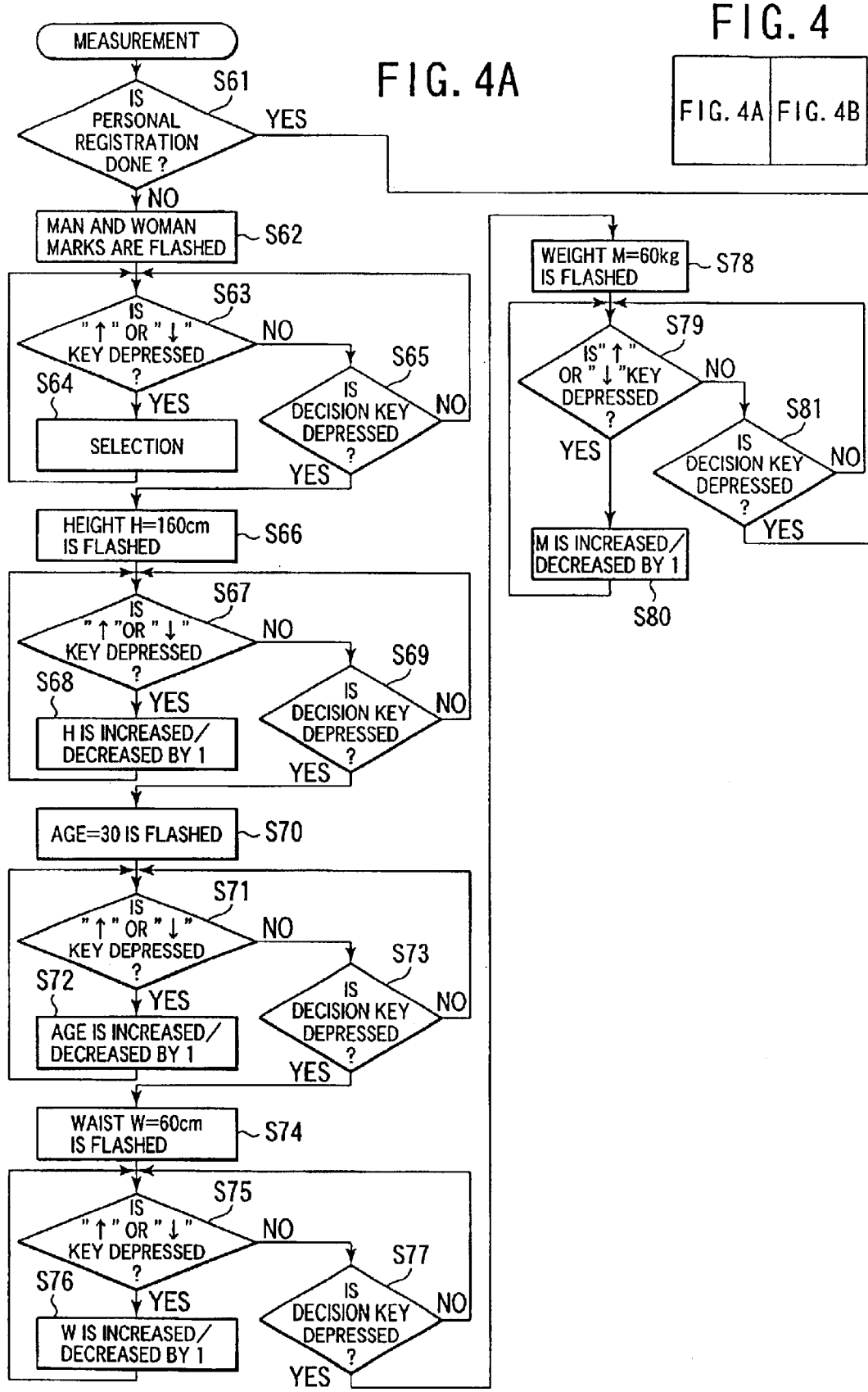
FIG. 4 is a flow chart illustrating a measurement routine for the visceral fat estimation apparatus in FIG. 1.
Figure 4B:
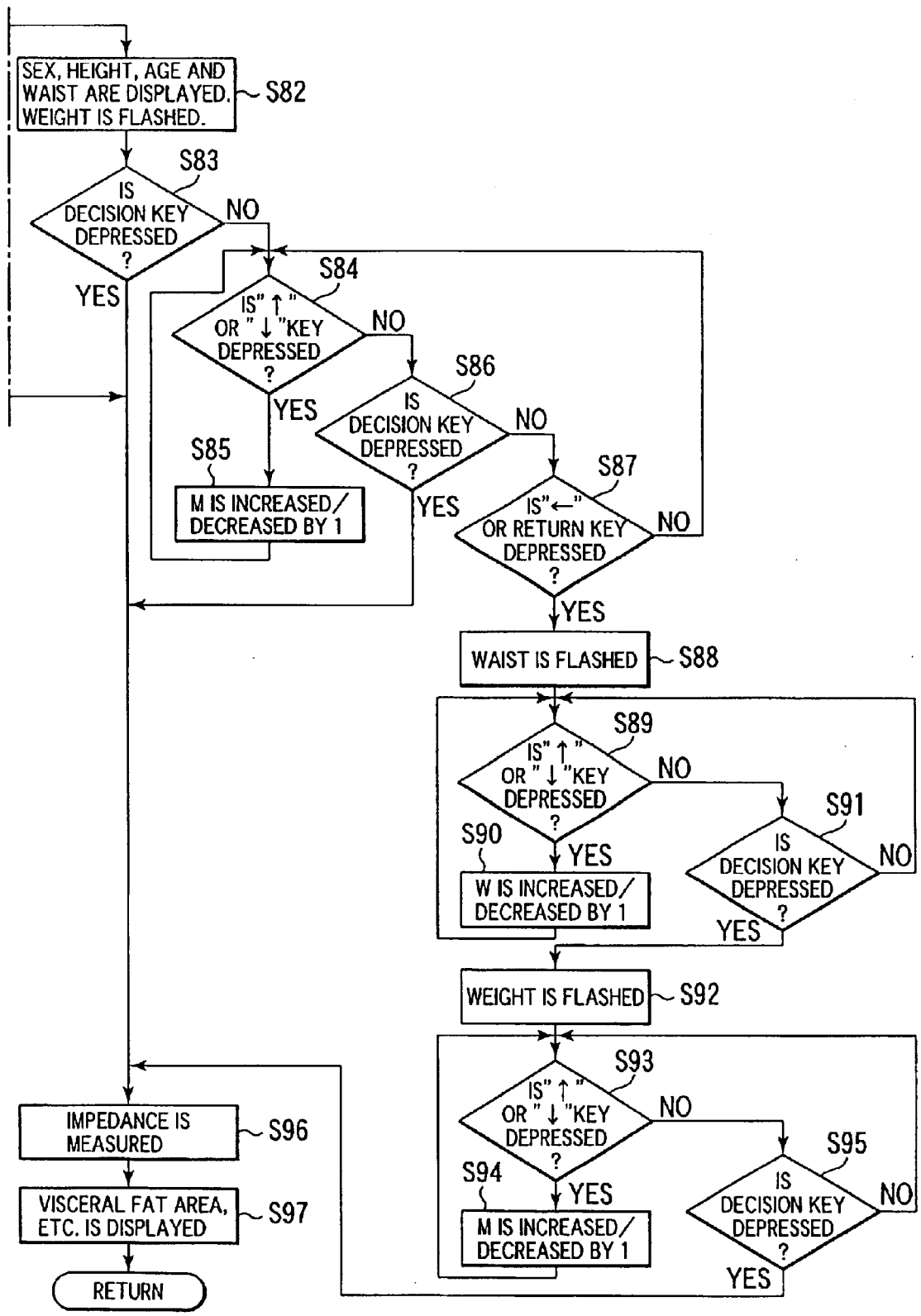

FIG. 4 is a flow chart illustrating a measurement routine when the measurement key 48 is depressed. At step S61 a check is made to determine whether registration of a person to be measured has been done. If so, the routine proceeds to step S82. At step S62 the display section 44 flashes man and woman marks. At step S63 it is determined whether any one of "↑" key 45U or "↓" key 45D is depressed. If not, the routine proceeds to step S65. At step S64 a man or a woman is selected. At step S65 it is determined whether the decision key 47 is depressed or not. If not, the routine returns to step S63.

At step S66 the display section 44 flashes "Height "H"= 160 cm". At step S67 it is determined whether any one of "↑" key 45U or "↓" key 45D is depressed. If not, the routine proceeds to step S69. If "↑" key 45U is depressed in step S68 then "H" is increased by one. But, if "↓" key 45D is depressed then "H" is decreased by one. The routine returns to step S67. If the decision key 47 is not depressed in step S69 then the routine returns to step S67. At steps S70 to S81 setting of the age "Age", the waist size "W" and the body weight "M" is performed in the same manner as that of the height. Thereafter, the routine proceeds to step S96.

Figures 10A, 10B, 11:
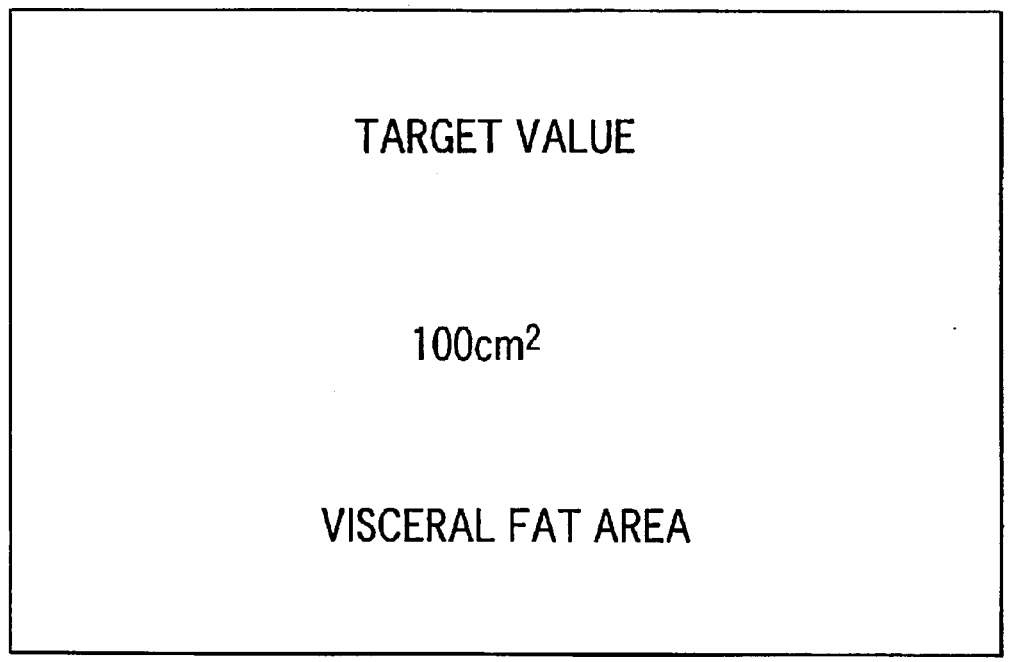
FIGS. 10A and 10B show one example of display of input and output values in the visceral fat estimation apparatus in FIG. 1.
FIG. 11 shows one example of display of target for diet in the visceral fat estimation apparatus in FIG. 1.

At step S82 the sex, height "H", age "Age" and waist size "W" of the registered personal data are displayed on the display section 44, as shown in FIG. 10A. The body weight "M" is flashed. At step S83 it is determined whether the decision key 47 is depressed or not. If so, the routine proceeds to step S96. At step S84 it is determined whether any one of "↑" key 45U or "↓" key 45D is depressed. If not, the routine proceeds to step S86. If the "↑" key 45U is depressed then "M" is increased by one in step S85. But, if the "↓" key 45D is depressed then "M" is decreased by one. The routine returns to step S84. If the decision key 47 is depressed in step S86 then the routine proceeds to step S96. If the "←" key 45L or the return key 46 is not depressed in step S87 then the routine returns to step S84. At steps S88 to S95 setting of the waist size "W" and the body weight "M" is performed in the same manner as above.

At step S96 measurement of the impedance is performed. The left thumb finger of the person to be measured is contact with the current supplying electrode 42a, the right thumb finger is contact with the current supplying electrode 42b, the left palm is contact with the voltage detection electrode 43a, and the right palm is contact with the voltage detection electrode 43b. When measurement is started the RF constant current circuit 67 produces a weak RF constant current output "I". This current output is applied to the person to be measured via the current supplying electrodes 42a, 42b. The current flowing through the body of the person at this time is detected by the voltage measurement circuit 68 as the living body potential difference between the voltage detection electrodes 43a, 43b. This analog output signal is converted into the digital signal "V" in the A/D converter circuit 69. Then, the impedance is calculated by the formula "voltage V÷current I".

At step S97 the body fat rate and the visceral fat area "Y" are calculated and displayed on the display section 44, as shown in FIG. 10B. It is well known that the body fat rate for a whole body is derived from the impedance between both hands according to the correlation formula. A multiple regression analysis is applied with an objective variable of "Y" and descriptive variables of height "H", body weight "M" and waist size "W" to produce a regression formula that is stored in the memory 65 in advance and is used to derive a visceral fat area "$Y_1$" as follows:

$$Y_1 = C_1 \times \text{height"}H\text{"} + C_2 \times \text{body weight"}M\text{"} + C_3 \times \text{waist size"}W\text{"} + C_4 \times \text{body fat mass"}F\text{"} + C_5 \quad (1)$$

The age may additionally be included as follows:

$$Y_2 = C_{21} \times \text{height"}H\text{"} + C_{22} \times \text{body weight"}M\text{"} + C_{23} \times \text{waist size"}W\text{"} + C_{24} \times \text{body fat mass"}F\text{"} + C_{25} \times \text{age"Age"} + C_{26} \quad (2)$$

Alternatively, the waist size "W" may be omitted, but instead, the body mass index "BMI" may be included as follows:

$$Y_3 = C_{31} \times \text{"}BMI\text{"} + C_{32} \times \text{body fat mass"}F\text{"} + C_{33} \quad (3)$$

Where "BMI"=body weight (kg)÷height (m)÷height (m).

Figure 5:
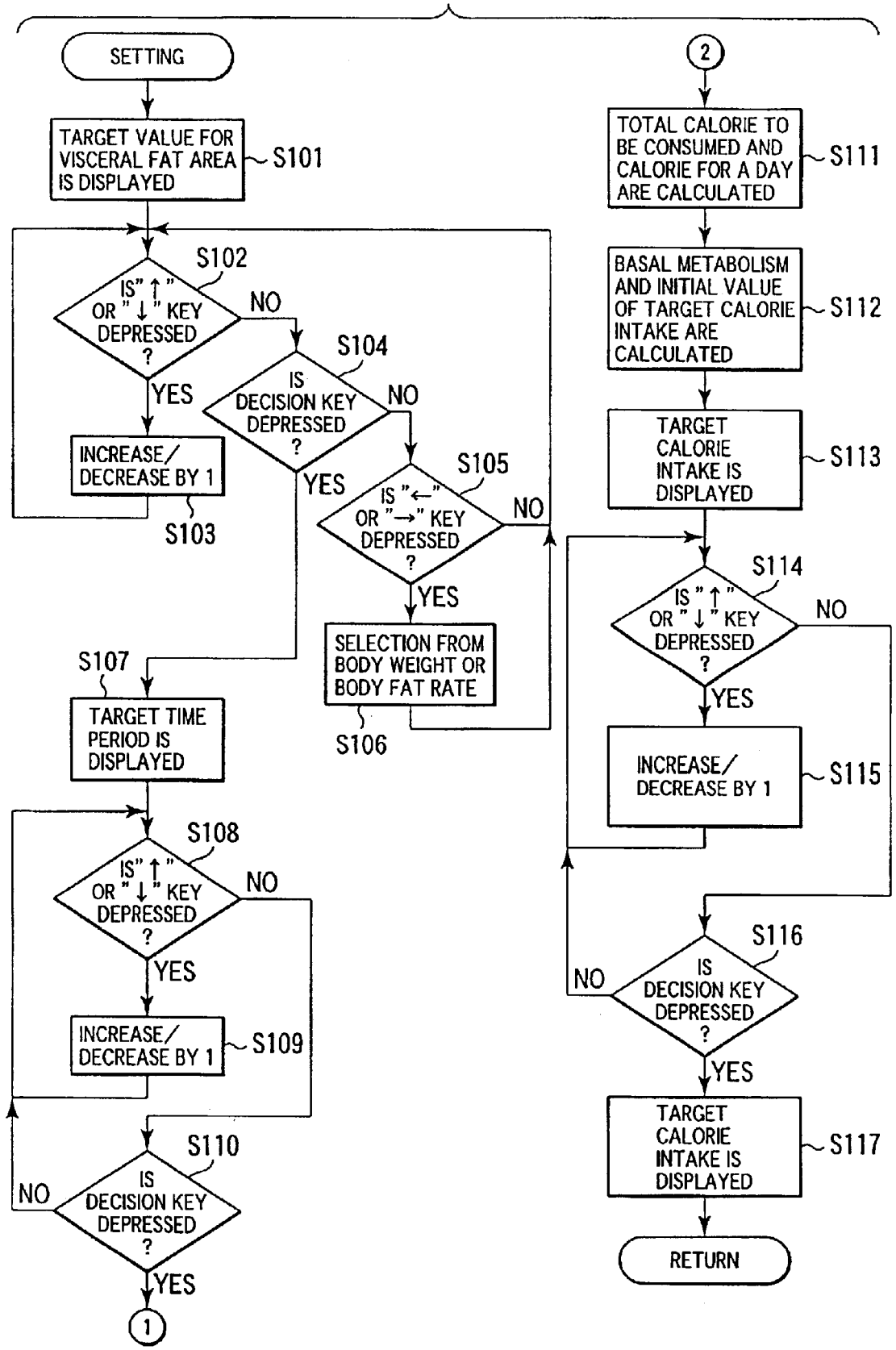
FIG. 5 is a flow chart illustrating a setting routine for the visceral fat estimation apparatus in FIG. 1.

FIG. 5 is a flow chart illustrating a setting routine when the set key 49 is depressed. Here, either one of visceral fat area, body weight or body fat rate is selected as the target parameter for diet and setting of the target value is performed. Initially, before the set key 49 is depressed, it is determined whether the measurement key has been depressed and the measurement process has been done. If not, a message "depress the measurement key and perform the measurement process" is displayed on the display section 44, and the sub-routine is ended. At step S101 the target value of visceral fat area Y=100 cm$_2$ is displayed on the display section 44, as shown in FIG. 11. At step S102 it is determined whether any one of "↑" key 45U or "↓" key 45D is depressed. If not, the routine proceeds to step S104. If the "↑" key 45U is depressed in step S102 then the target value for visceral fat area is increased by one. But, if the "↓" key 45D is depressed then the target value for visceral fat area is decreased by one. The routine returns to step S102.

At step S104 it is determined whether the decision key 47 is depressed or not. If so, the routine proceeds to step S107. At step S105 it is determined whether any one of "←" key 45L or "→" key 45R is depressed. If not, the routine proceeds to step S102. At step S106 either one of the body weight or the body fat rate is selected as the target parameter. The routine proceeds to step S102.

At step S107 the time period during which the target value is to be attained is displayed on the display section 44 as "P=30 days". At step S108 it is determined whether any one of "↑" key 45U or "↓" key 45D is depressed. If not, the routine proceeds to step S110. If the "↑" key 45U is depressed then the target time period is increased by one in step S109. But, if the "↓" key 45D is depressed then the target time period is decreased by one. The routine returns to step S108. At step S110 it is determined whether the decision key 47 is depressed or not. If not, the routine returns to step S108.

At step S111 the total calorie to be consumed in order to attain the target value for visceral fat area, body fat rate or body weight is calculated. The body fat mass to be reduced is calculated from the visceral fat area to be reduced. The body fat mass to be reduced is also calculated from the body fat rate to be reduced. The body fat mass is additionally calculated from the body fat rate and the body weight to be reduced. There is a uniquely defined relationship between the body fat rate to be reduced and the calorie to be consumed, which relationship is used to derive the total calorie to be consumed due to an exercise. Then, based on this total calorie and the target time period "P", the calorie to be consumed due to an exercise for a day is calculated. Thereafter, an initial setting of the variable (or calorie to be consumed due to an exercise) is performed using the following formula:

(Calorie to be consumed due to an exercise)=(Calorie to be consumed due to an exercise for a day)

At step S112 basal metabolism is calculated. Because the basal metabolism is proportional to fat free mass it can be calculated from the fat free mass and the personal parameter. By its definition the fat free mass is calculated using the formula "body weight×(1−body fat rate)". Then, the initial value of target calorie intake is calculated. In this embodiment the ideal calorie intake is used as the initial value. The ideal calorie intake can be derived from the energy requirement per body weight. In this connection it has been known that the energy requirement per body weight is determined based on intensity in living activity, age and sex of a person to be measured.

At step S113 the initial value of target calorie intake calculated in the previous step is displayed on the display section 44. At step S114 it is determined whether any one of "↑" key 45U or "↓" key 45D is depressed. If not, the routine proceeds to step S116. If the "↑" key 45U is depressed then the target calorie intake is increased by one in step S115. This slightly higher calorie setting is to be attained mainly by calorie consumption as the result of an exercise. But, if the "↓" key 45D is depressed then the target calorie intake is decreased by one. This slightly lower calorie setting is to be attained mainly by a diet. At step S116 it is determined whether the decision key 47 is depressed or not. If not, the routine returns to step S114. At step S117 the target calorie intake is set as the initial value of the variable (allowable calorie intake) and is displayed on the display section 44. Thereafter, if no key is depressed within the predetermined period, the power supply is automatically turned OFF.

Basically, in this apparatus, the target calorie intake is never set at the value lower than the ideal calorie intake. The reason for which is as follows: If it is attempted to reduce the body fat simply by the diet then not only the fat but also the muscle and the bone would be reduced. Reduction of muscle causes reduction of basal metabolism of the whole body, and as the result, the body weight becomes difficult to reduce so that even slight overeating makes to grow fat. However, the present apparatus has additional capability of adjusting the target calorie intake for the sake of a person who wants to reduce the target calorie intake irrespective of taking into account of such fact.

Figure 6:
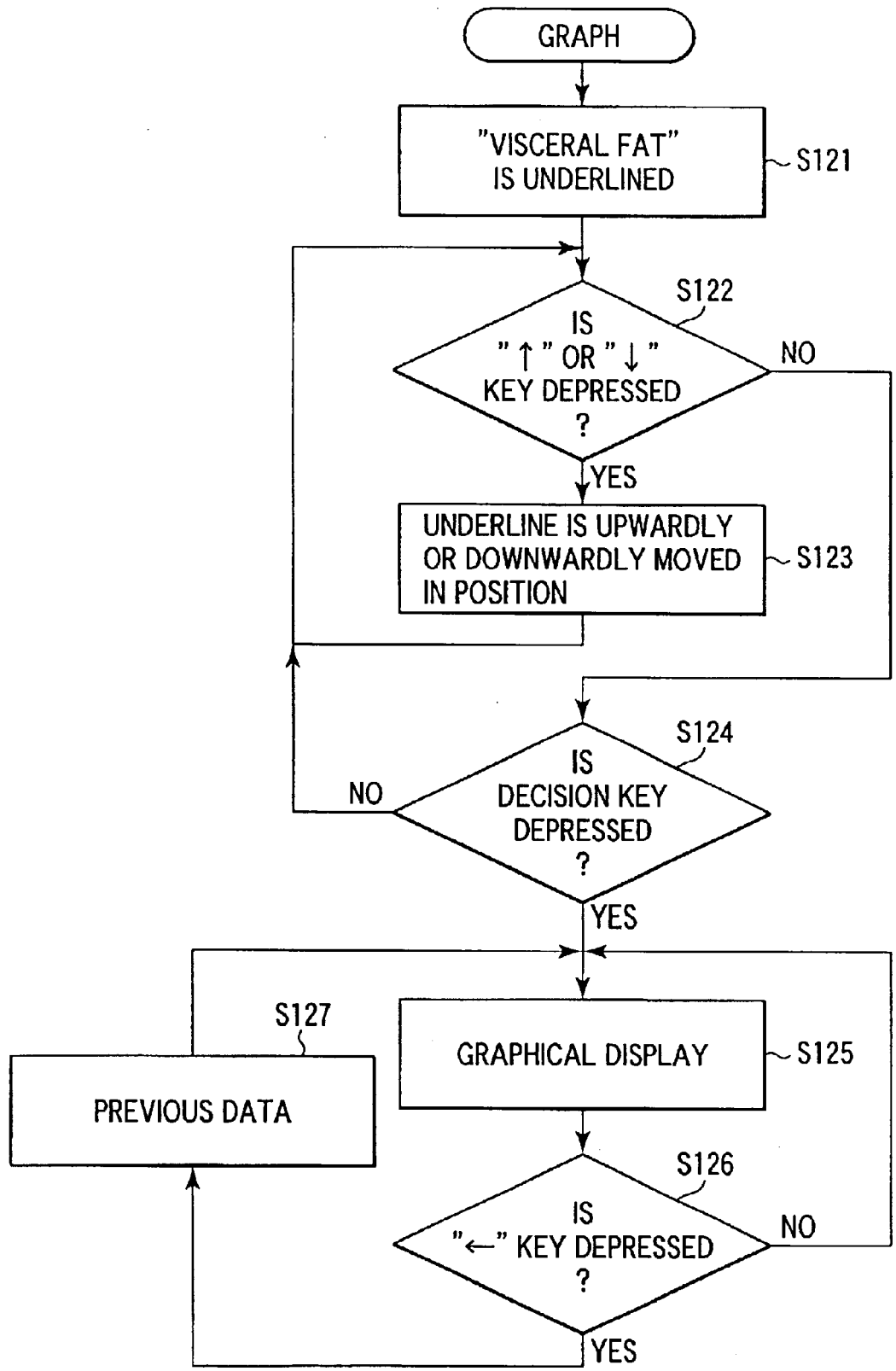
FIG. 6 is a flow chart illustrating a graphic display routine for the visceral fat estimation apparatus in FIG. 1.
Figure 12A:
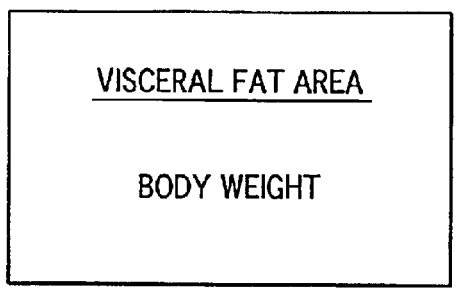
FIGS. 12A and 12B graphically show visceral fat area in the visceral fat estimation apparatus in FIG. 1.

FIG. 6 is a flow chart illustrating a graphic display routine when the graph key 50 is depressed. The routine produces a graph showing any daily change in visceral fat area, body weight and body fat rate. When the graph key 50 is depressed the display section 44 displays a screen as shown in FIG. 12A in step S121. The display "visceral fat area" is underlined. At step S122 it is determined whether any one of "↑" key 45U or "↓" key 45D is depressed. If not, the routine proceeds to step S124. If the "↓" key 45D is depressed then the underline is downwardly moved in position in step S123. That is to say, the display "body weight" is underlined. If the "↓" key 45D is depressed once again then the underline is further downwardly moved in position so that the display "body fat rate" is underlined. Inversely, if the "↑" key 45U is depressed the underline is upwardly moved in position.

Figure 12B:
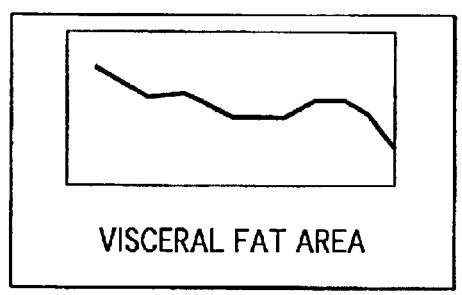

At step S124 it is determined whether the decision key 47 is depressed. If not, the routine returns to step S122. At step S125 the daily change for the underlined item is graphically displayed. The screen as shown in FIG. 12B shows the case where the underlined item is visceral fat area. At step S126 it is determined whether the "←" key 45L is depressed. If not, the routine returns to step S126. At step S127 the data displayed is replaced with the previous data that has been displayed just before. The routine returns to step S125.

Figure 7:
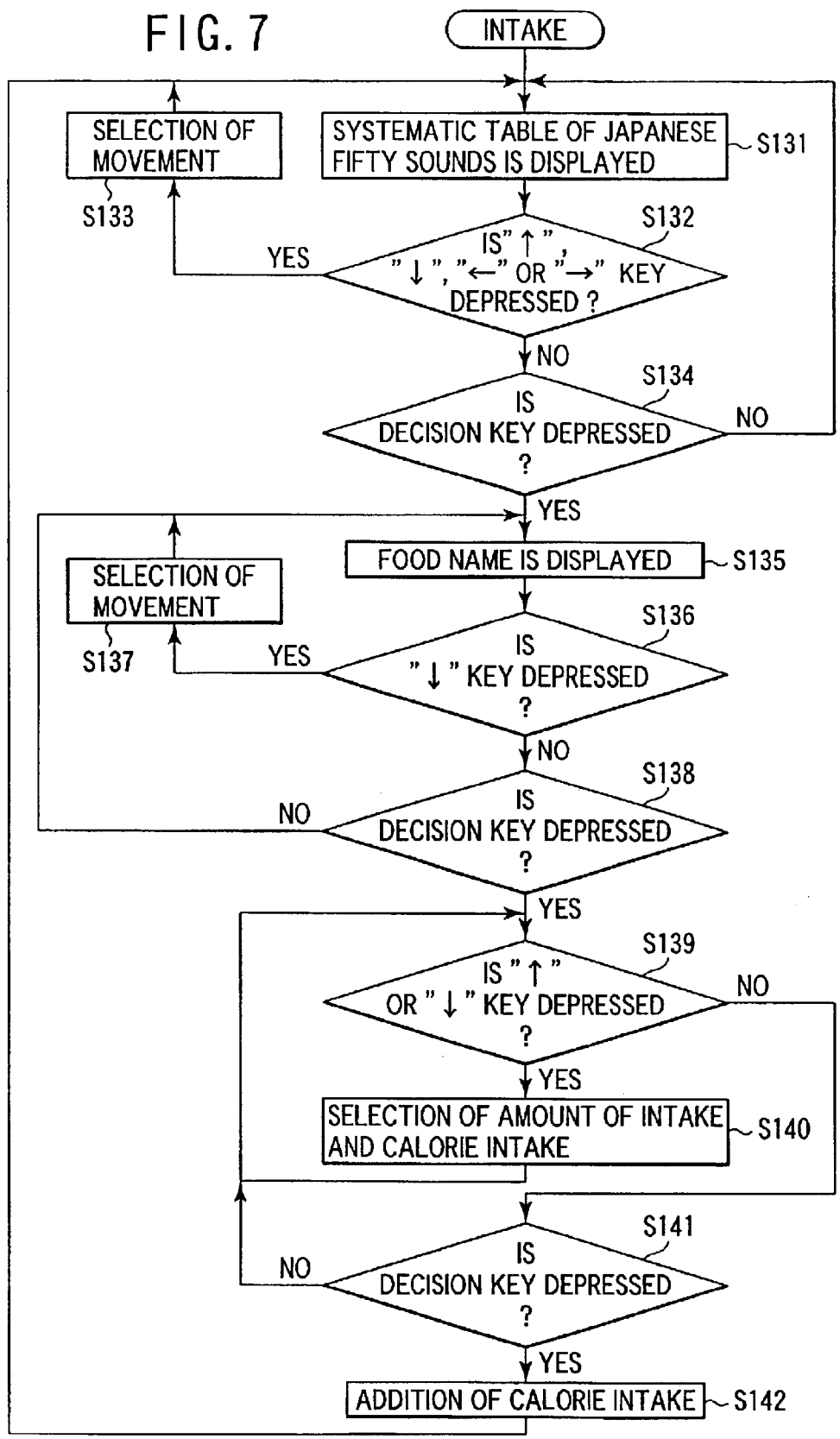
FIG. 7 is a flow chart illustrating a calorie intake calculation routine for the visceral fat estimation apparatus in FIG. 1.
Figure 13A:
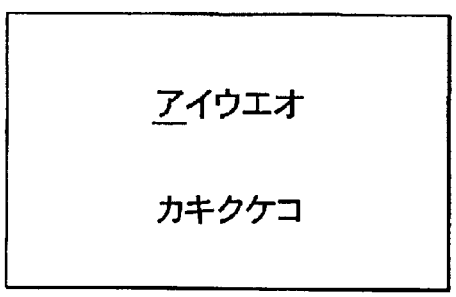
FIGS. 13A and 13B show one example of display of food name and amount of intake for that food.

FIG. 7 is a flow chart illustrating an intake process routine when the intake key 51 is depressed. The routine calculates the calorie intake given by some food selected. When the intake key 51 is depressed then a systematic table of Japanese fifty sounds is displayed on the display section 44 to select the food, as shown in FIG. 13A, at step S131. An underlined row of characters is selected. In the case as shown in FIG. 13 a row beginning with a character "A" is selected. At step S132 it is determined whether any one of the "↑" key 45U, "↓" key 45D, "→" key 45R or "←" key 45L is depressed. If not, the routine proceeds to step S134. But, if so, the underline is moved in upward, downward, right-hand or left-hand direction by one position. The routine returns to step S131.

Figure 13B:
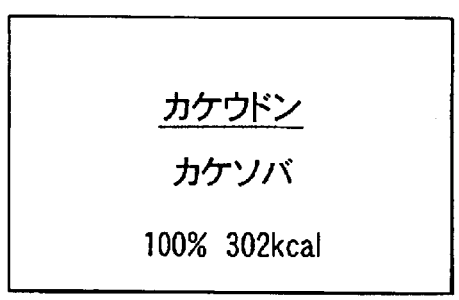

At step S134 it is determined whether the decision key 47 is depressed or not. If not, the routine returns to step S131. At step S135 the food name whose first character is one that is selected is displayed, as shown in FIG. 13B. In this example a character "Ka" is selected, and as the result, the food name "Kakeudon(noodle in soup)" that begins with "Ka" selected is displayed with the underline. At step S136 it is determined whether the "↓" key 45D is depressed or not. If not, the routine proceeds to step S138. At step S137 the underline is moved in downward direction by one position. The routine returns to step S135. At step S136 an additional decision may arbitrarily be performed to determine whether the "↑" key 45U is depressed. In this case it is possible to correct the position of the underline if the "↓" key 45D is depressed too many.

At step S138 it is determined whether the decision key 47 is depressed. If not, the routine returns to step S135. At step S139 it is determined whether the "↑" key 45U or "↓" key 45D is depressed. If not, the routine proceeds to step S141. But, if the "↑" key 45U is depressed, the amount of intake (%) displayed at lower left position of the screen of the display 44 is increased to "110%", for example, at step S140. Instead, if the "↓" key 45D is depressed, it is decreased to "90%", for example. For the food that is selected at step S137, the calorie intake corresponding to the amount of intake as assigned at step S140 is calculated and the result is displayed at lower right position of the screen of the display 44. In this connection, it is assumed that a list representing the relationship between each of the foods and the corresponding calorie value per a food unit (100%) is stored in the memory 65 in advance. In this example, as shown in FIG. 13B, a bowlful of "Kakeudon (noodle in soup)" (100%) is stored in the memory 65, together with the corresponding value of "302 kcal". Then the routine returns to step S139.

At step S141 it is determined whether the decision key 47 is depressed. If not, the routine returns to step S139. At step S142 the finally determined calorie intake is added to the value of calorie intake variable stored in the memory 65. Then, the remaining allowable calorie intake is updated according to the following formula:

(Remaining allowable calorie intake)=(Total allowable calorie intake)−(Actual calorie intake)

The routine returns to step S131 for displaying a systematic table of Japanese fifty sounds.

Figure 8:
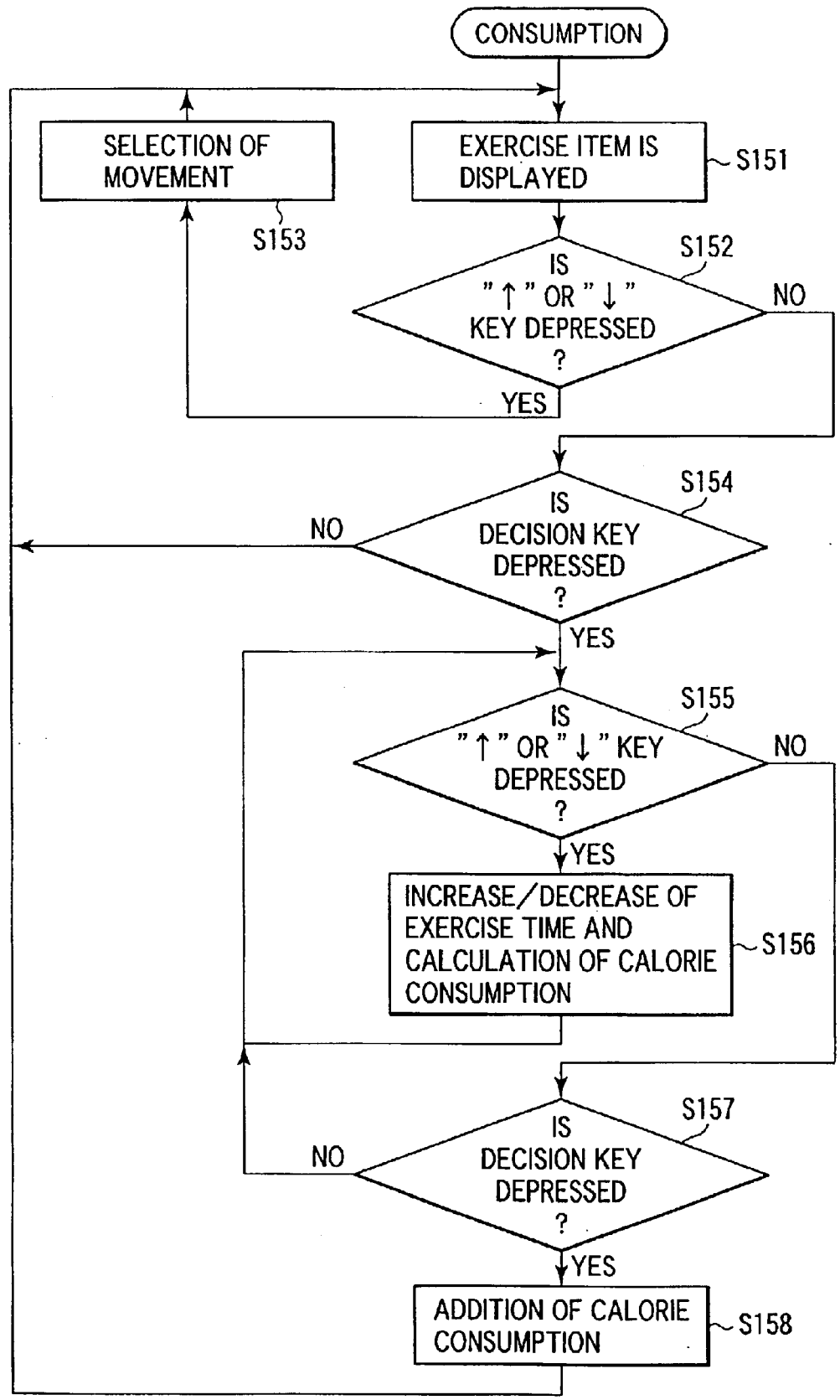
FIG. 8 is a flow chart illustrating a calorie consumption processing routine for the visceral fat estimation apparatus in FIG. 1.
Figure 14:
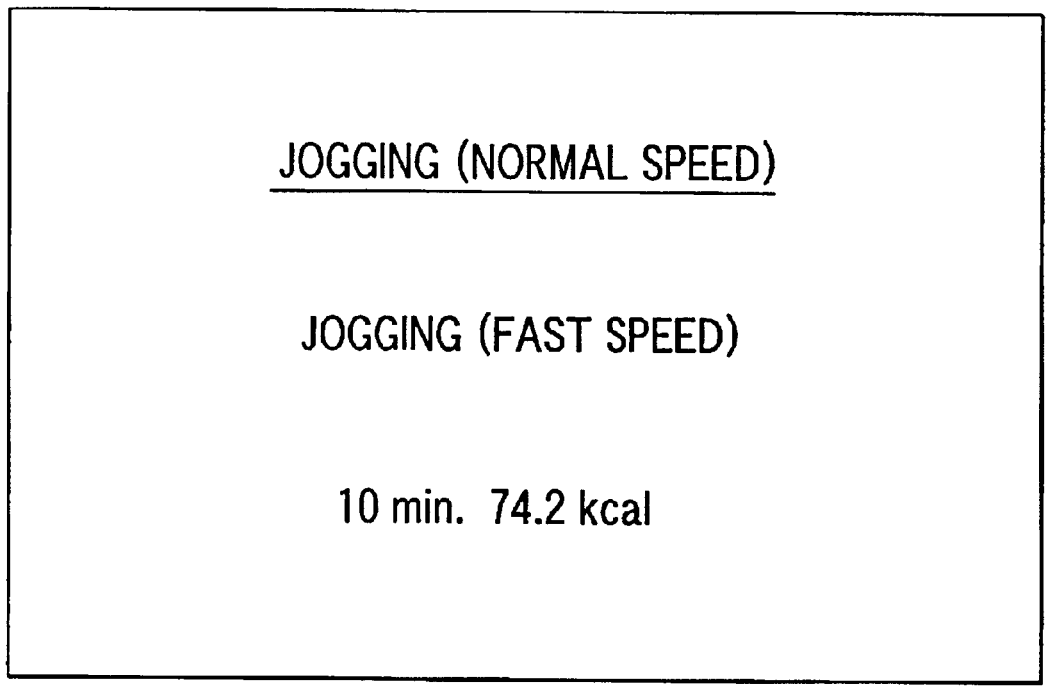
FIG. 14 shows one example of display of calorie consumption due to exercise.

FIG. 8 is a flow chart illustrating a consumption processing routine if consumption key 52 is depressed. This routine calculates the calorie consumption due to an exercise assigned. If the consumption key 52 is depressed the exercise items are sequentially displayed in the order of Japanese fifty sounds on the display 44, at step S151, as shown in FIG. 14. The exercise items selected is indicated by an underline. At step S152 it is determined whether the "↑" key 45U or "↓" key 45D is depressed. If not, the routine proceeds to step S154. But, if the "↑" key 45U is depressed, the underline is moved upwardly by one position in step S153. Instead, if the "↓" key 45D is depressed, the underline is moved downwardly by one position. The routine returns to step S151.

At step S154 it is determined whether the decision key 47 is depressed. If not, the routine returns to step S151. At step S155 it is determined whether the "↑" key 45U or "↓" key 45D is depressed. If not, the routine proceeds to step S157. If the "↑" key 45U is depressed the time duration of exercise displayed at lower left of the screen of the display 44 is increased, at step S156. But, if the "↓" key 45D is depressed, it is decreased. The calorie to be consumed due to the exercise selected at step S153 during the time duration assigned at step S156 is calculated and the result is displayed at lower right of the screen of the display 44. In this connection it is assumed that a list representing the relationship between each of the exercise items and the corresponding calorie consumption per one min. of exercise and per 1 kg of body weight is stored in the memory 65 in advance. In the example of FIG. 14, a "jogging (normal speed)" is stored in the memory 65, together with the corresponding calorie consumption of "0.117 kcal/kg/min." In view of the body weight of the person to be measured, as shown in FIG. 10A, the calorie consumption due to the exercise during 10 min. is calculated to be 74.2 kcal. Then, the routine returns to step S155.

At step S157 it is determined whether the decision key 47 is depressed. If not, the routine returns to step S155. At step S158 the finally determined calorie consumption is added to the value of calorie consumption variable stored in the memory 65. Then, the remaining calorie consumption is updated according to the following formula:

(Remaining calorie consumption)=(Total calorie consumption)−(Actual calorie consumption)

Then, the routine returns to step S151.

Figure 9:
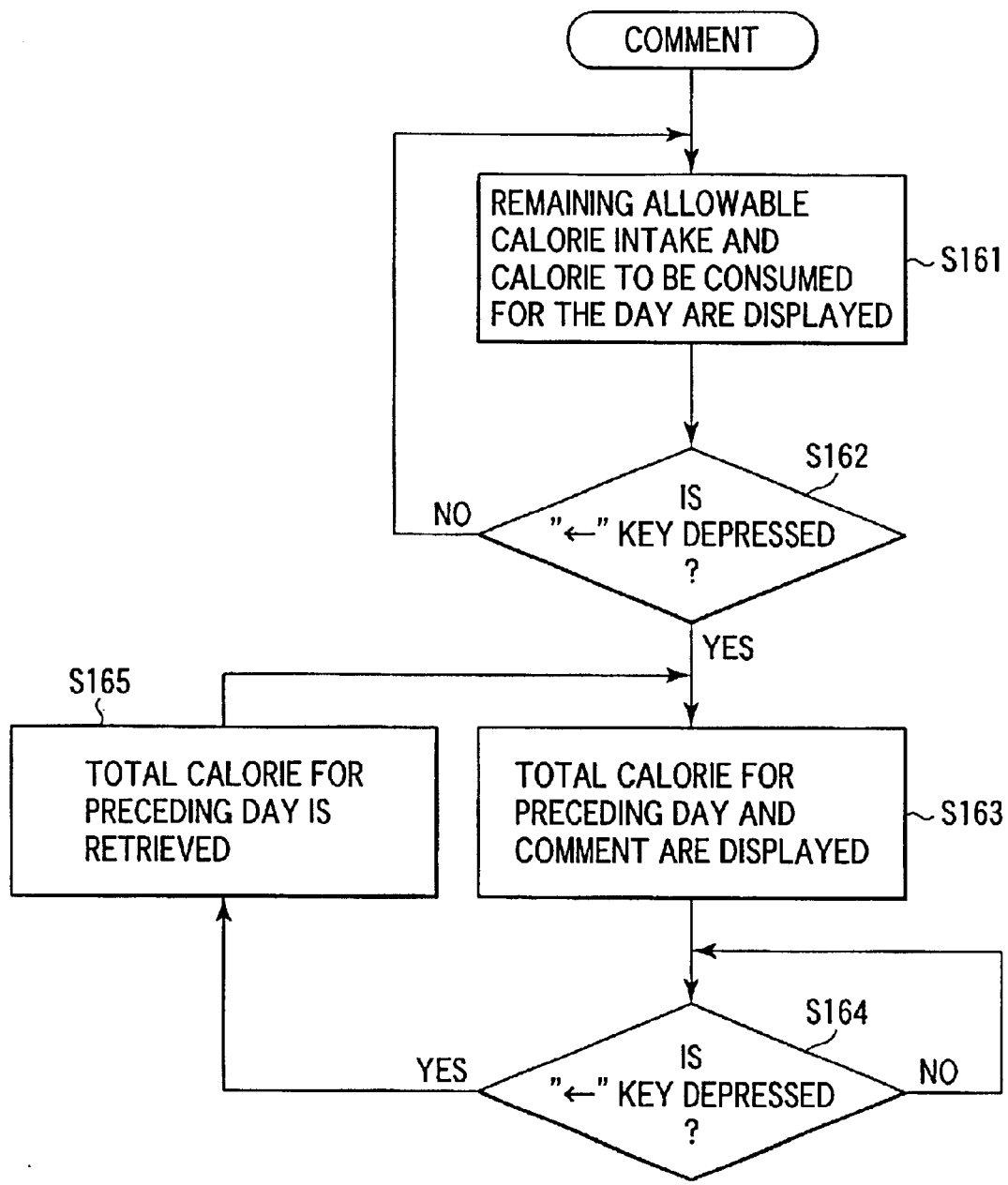
FIG. 9 is a flow chart illustrating a comment processing routine for the visceral fat estimation apparatus in FIG. 1.

FIG. 9 is a flow chart illustrating a comment processing routine if a comment key 53 is depressed. The data including the remaining allowable calorie intake and the remaining calorie consumption due to exercise for that day after the time that the comment key 53 is depressed is displayed on the display section 44. In addition, the total calorie value for the preceding day and some message such as "Lack of exercise" are also displayed. Initially, before depression of the comment key 53, it is determined whether the measurement key has been depressed for measurement process. If not, the message "Depress the measurement key for measurement process" is displayed on the display section 44. Then, the subroutine is terminated.

Figure 15A:
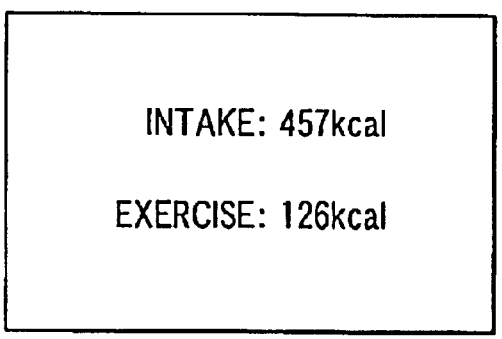
FIGS. 15A and 15B show one example of display of comment.

At step S161 the remaining allowable calorie intake and the remaining calorie consumption due to exercise after the current time is displayed on the display section 44, as shown in FIG. 15A.

At step S162 it is determined whether the "←" key 45L is depressed. If not, the routine returns to step S161. At step S163 the total calorie for the preceding day and some message is displayed. The total calorie for the preceding day is calculated by the following formula:

(Total calorie for preceding day)=(Calorie intake for preceding day)−(Calorie consumption due to exercise for preceding day)−(Basal metabolism)

Where the basal metabolism is one that is calculated at step 112 in the flow chart of FIG. 5.

Figure 15B:
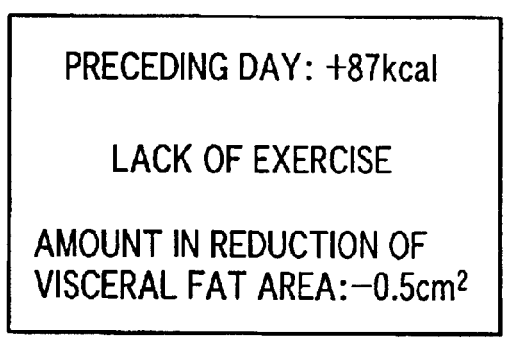
Figure 16A:
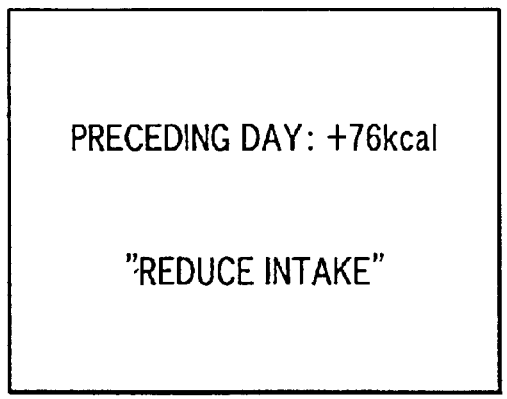
FIGS. 16A to 16F show another example of display of comment.
Figure 16B:
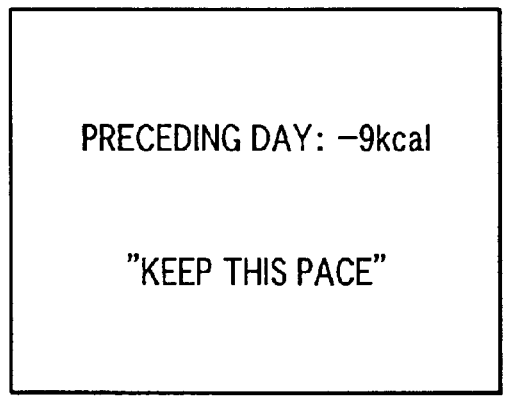
Figure 16C:
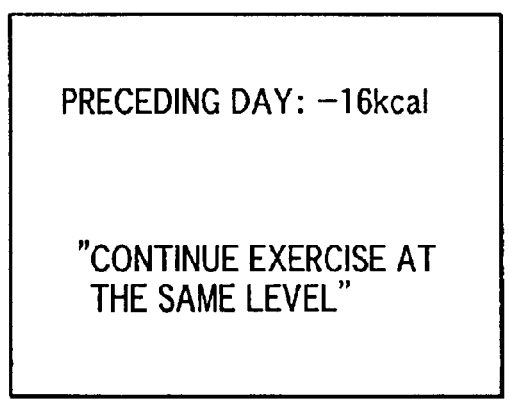
Figure 16D:
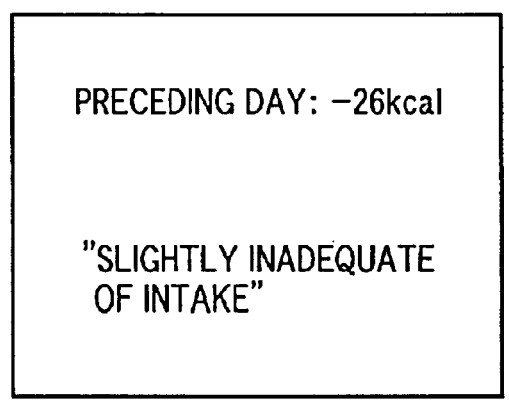
Figure 16E:
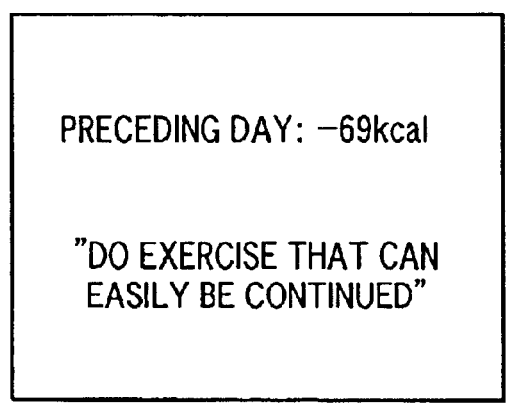
Figure 16F:
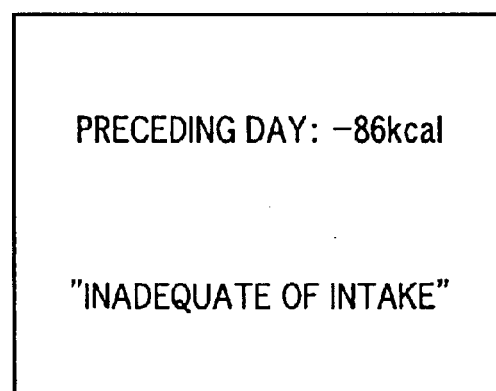

Examples of the comment according to the total calorie thus obtained are shown in FIG. 15B and FIGS. 16A to 16F. If the total calorie has a positive value the message "Lack of exercise" is displayed; if it has zero or a negative smaller value the message "Continue exercise at the same level" is displayed; or if it has a negative larger value the message "Inadequate intake" is displayed. In view of the intake process described with reference to FIG. 7 and the consumption process described with reference to FIG. 8, the person to be measured can understand the relationship between the amount of intake of food and the corresponding calorie intake, and the relationship between the degree of exercise and the corresponding calorie consumption. Therefore, by displaying the total calorie and the comment, the person to be measured can easily know the target value for amount of intake of food and for degree of exercise that he should increase. Furthermore, an amount in decrease of visceral fat area is also displayed, as shown in FIG. 15B. In this case the negative value means that the visceral fat area has been increased. The amount in decrease of visceral fat area is one that is calculated based on the total calorie. By this display the person to be measured can know the relationship between the total calorie and the visceral fat area. That is to say, the person to be measured can know how much amount the visceral fat area he can decrease by how much degree the exercise he does.

At step S164 it is determined whether the "←" key 45L is depressed. If not, the routine returns to step S164. At step S165 the calorie intake and the calorie consumption for a preceding day is retrieved from the memory 65. The routine returns to step S163.

If, before depression of the comment key 53, the setting key 49 has not been depressed, and therefore, the target values for visceral fat area, etc. have not been set, then, before step S161, the target value for visceral fat area is set at some standard value and the target time period is set at some reasonable and standard diet time period, and thereafter, the data including the total calorie consumption, the calorie consumption per a day, the basal metabolism, the target calorie intake and the target calorie consumption is calculated, as shown in FIG. 5.

In the process as described above, if there is no key input within the predetermined time period, the power supply is automatically turned OFF.

In the embodiment as described above, the personal data of height, age, etc. can be registered only for one person. In another embodiment, however, the personal data for plural persons may be registered by providing a plurality of keys each for each person. More particularly, when a personal data for a person is entered the corresponding personal key is depressed and the personal data is stored in an area within the memory corresponding to that person. Thereafter, when it is desired to utilize the data for that person, it is retrieved from the area within the memory simply by depressing the personal key for that person.

In the embodiment as described above, the height data has been manually entered via the key device. But, some height measurement device may be included in order to automatically enter the height data. Furthermore, in the above embodiment, the body fat rate has been calculated based on the measurement of bioelectrical impedance. However, it may manually be entered, as in the case of the height data that has been manually entered via the key device.

Figure 17:
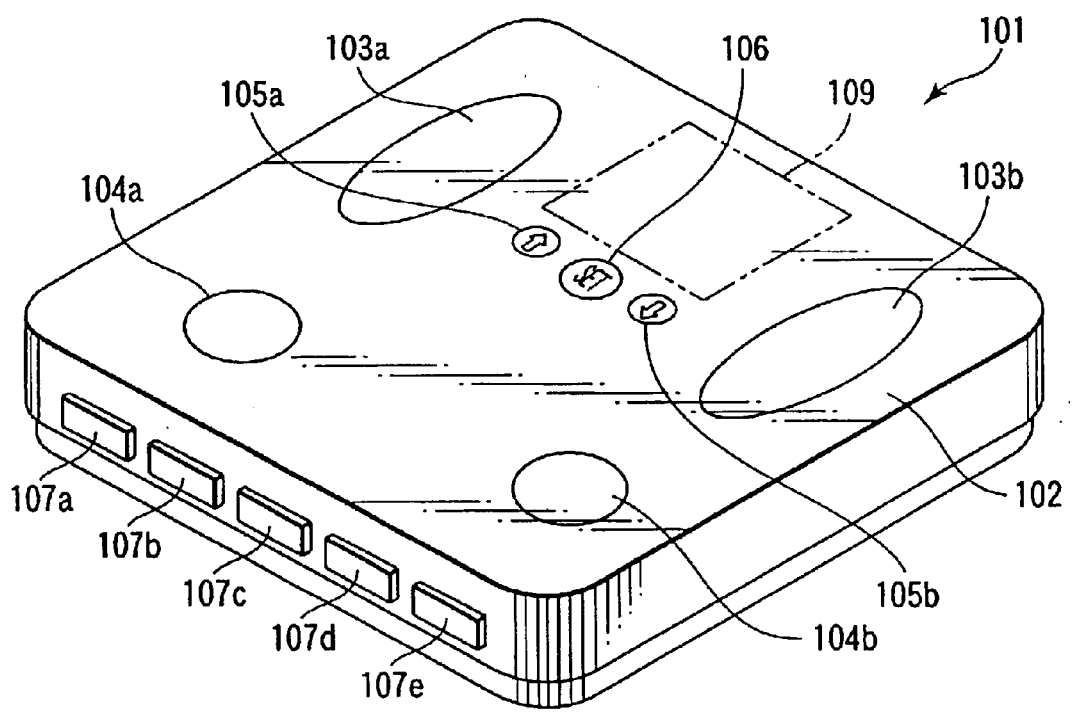
FIG. 17 is a perspective view illustrating an apparatus including a bioelectrical impedance measurement section separated from the apparatus in FIG. 1; and a body weight measurement section.

Moreover, in the above embodiment, the body weight of a person has been manually entered via the key device. However, the apparatus in FIG. 1 may be modified to automatically enter the body weight by connecting a body weight measurement device 101 as shown in FIG. 17 with the apparatus in FIG. 1 by means of a wireless communication using infrared ray or electromagnetic wave or of an electrical cable. In particular, referring to FIG. 17, the body weight measurement device 101 includes: current supplying electrodes 103a, 103b and voltage measurement electrodes 104a, 104b; a current supplying circuit within a measurement platform 102 for passing lower constant current between the current supplying electrodes 103a, 103b; a voltage measurement circuit for measuring the voltage across the voltage measurement electrodes 104a, 104b; and an arithmetic circuit for calculating bioelectrical impedance between both feet of the person depending on the constant current and the voltage, which enables to derive the visceral fat area or the body fat rate from the bioelectrical impedance calculated. In this case the electrodes 42a, 42b, 43a, 43b for measuring the bioelectrical impedance between both hands of the person in FIG. 1 may be omitted. The CPU 64 in FIG. 2 calculates the visceral fat area or the body fat rate based on the bioelectrical impedance measured by the body weight measurement device 101.

Further referring to FIG. 17, the body weight measurement device 101 also includes: a set key 106 for setting the personal data such as height, age, sex, etc.; an UP key 105a for increasing the numerical value; a DOWN key 105b for decreasing the numerical value; personal keys 107a to 107e for registering or reading out the personal data; and a display section 109 for displaying the set conditions, measurement results or evaluation results. Therefore, the body weight measurement device 101 can act alone as the visceral fat estimation device without the visceral fat estimation apparatus 41. If there is no need of such usage of the body weight measurement device 101 those components may, of course, be omitted.

The visceral fat estimation apparatus according to the present invention is not limited to the embodiment as above, but various modifications may be made without departing from the scope of the present invention as defined in the claims.

It is apparent from the foregoing that a visceral fat estimation apparatus according to the present invention can determine the calorie to be consumed for a day due to an exercise, based on any one of targets for visceral fat area, body fat rate and body weight, and a time period during which the target is to be attained, whereby if a person to be measured falls within the region of adiposity then the target value of visceral fat area can be set, and the calorie intake and the calorie consumption can be controlled to attain said target value.

What is claimed is:

1. A visceral fat estimation apparatus, comprising:

an input device;

an estimation device;

a calorie consumption determination device;

an exercise item selection and determination device;

an exercise time duration determination device;

a calorie consumption update device;

a target calorie intake determination device;

a food name selection and determination device;

an intake amount determination device;

an allowable calorie intake update device; and a display device, wherein said input device is for entering at least height, body weight and body fat rate of a person to be measured;

said estimation device estimates a visceral fat area based on the input value entered by said input device;

said calorie consumption determination device determines a calorie amount to be consumed by exercise for a day based on a visceral fat area to be reduced from said visceral fat area estimated by said estimation device;

said exercise item selection and determination device comprises exercise item altering and decision keys and selects and determines an exercise item to be done using the exercise item altering and decision keys;

said exercise time duration determination device comprises exercise time altering and decision keys and determines an exercise time duration using the exercise time altering and decision keys;

said calorie consumption update device determines a calorie consumption based on said exercise item determined by said exercise item selection and determination device and said exercise time duration determined by said exercise time duration determination device and updates said calorie amount to be consumed by exercise for a day by subtracting said determined calorie consumption from said calorie amount to be consumed by exercise for a day determined by said calorie consumption determination device;

said target calorie intake determination device comprises target calorie intake altering and decision keys determines a target calorie intake for a day using the target calorie intake altering and decision keys, based on the input value entered using said input device;

said food name selection and determination device comprises food name altering and decision keys and selects and determines a food name to be taken using the food name altering and decision keys;

said intake amount determination device comprises intake amount altering and decision keys and determines an intake amount using the intake amount altering and decision keys;

said allowable calorie intake update device determines a calorie intake based on said food name determined by said food name selection and determination device and said intake amount determined by said intake amount determination device and updates said allowable calorie intake for a day by subtracting said determined calorie intake from said allowable calorie intake for a day determined by said target calorie intake determination device; and said display device simultaneously displays said calorie amount to be consumed by exercise for a day and said allowable calorie intake for a day.

2. A visceral fat estimation apparatus according to claim 1, further comprising a target time period determination device, wherein said target time period determination device determines a time period during which the target value is to be attained, said calorie consumption determination device determines a body fat amount from said visceral fat area to be reduced, determines a total calorie amount to be consumed by exercise from said body fat amount and determines a calorie amount to be consumed by exercise for a day based on said total calorie to be consumed and said target time period determined by said target time period determination device.

3. A visceral fat estimation apparatus according to claim 1 or 2, in which said target calorie intake determination device comprises an initial value calculation unit and a modifying unit, wherein said initial value calculation unit calculates an initial value of said target calorie intake and said modifying unit modifies a value based on said initial value of target calorie intake.

4. A visceral fat estimation apparatus according to claim 3, in which said target calorie intake is an ideal calorie intake derived from the energy requirement per body weight.

5. A visceral fat estimation apparatus according to claim 1 or 2, further comprising a basal metabolism calculation unit and a total calorie calculation unit, wherein said basal metabolism calculation unit calculates a basal metabolism, said total calorie calculation unit calculates a total calorie amount by subtracting said calorie consumption for the preceding day determined by said calorie consumption update device and said basal metabolism calculated by said basal metabolism calculation unit from said calorie intake for the preceding day determined by said allowable calorie intake update device, and said display device further displays said total calorie amount calculated by said total calorie calculation unit.

6. A visceral fat estimation apparatus according to claim 5, in which said display device further displays an advice message on exercise or intake together with said total calorie amount.

7. A visceral fat estimation apparatus according to claim 1 or 2, in which said input device for entering the height is a height meter.

8. A visceral fat estimation apparatus according to claim 1 or 2, in which said input device for entering the height is a keying device that manually enters the height.

9. A visceral fat estimation apparatus according to claim 1 or 2, in which said input device for entering the body weight is a weight sensor.

10. A visceral fat estimation apparatus according to claim 1 or 2, in which said input device for entering the body weight is a keying device that manually enters the body weight.

11. A visceral fat estimation apparatus according to claim 1 or 2, in which said input device for entering the body fat rate is a body fat meter.

12. A visceral fat estimation apparatus according to claim 1 or 2, in which said input device for entering the body fat rate is a keying device that manually enters the body fat rate.

* * * * *